(12) United States Patent
Zadnikar et al.

(10) Patent No.: US 8,493,223 B2
(45) Date of Patent: Jul. 23, 2013

(54) SAFETY MONITORING SYSTEM

(75) Inventors: Matheus Zadnikar, Dilsen-Stokkem (BE); Rudi Vanderhenst, Overpelt (BE)

(73) Assignee: Z-Safety Systems N.V., Dilsen Stockkem (BE)

( * ) Notice: Subject to any disclaimer, the term of this patent is extended or adjusted under 35 U.S.C. 154(b) by 931 days.

(21) Appl. No.: 10/574,927

(22) PCT Filed: Oct. 7, 2003

(86) PCT No.: PCT/EP03/11089
§ 371 (c)(1),
(2), (4) Date: Apr. 24, 2007

(87) PCT Pub. No.: WO2005/041145
PCT Pub. Date: May 6, 2005

(65) Prior Publication Data
US 2007/0285222 A1  Dec. 13, 2007

(51) Int. Cl.
*G08B 17/10* (2006.01)
(52) U.S. Cl.
USPC ............ 340/632; 340/540; 340/603; 340/5.2; 340/5.28; 340/5.3; 356/213; 356/300; 73/23.2
(58) Field of Classification Search
USPC ........... 340/632, 603, 5.2, 5.3, 5.28; 356/213, 356/300; 73/23.2
See application file for complete search history.

(56) References Cited

U.S. PATENT DOCUMENTS

| 4,916,329 A | * | 4/1990 | Dang et al. .................. 307/66 |
| 5,045,839 A | * | 9/1991 | Ellis et al. ................. 340/539.11 |
| 5,382,943 A | * | 1/1995 | Tanaka ..................... 340/539.22 |
| 5,619,183 A | * | 4/1997 | Ziegra et al. ................. 340/505 |
| 5,771,004 A | | 6/1998 | Suppelsa et al. |
| 5,796,341 A | * | 8/1998 | Stratiotis .................... 340/573.1 |
| 5,844,601 A | * | 12/1998 | McPheely et al. ............ 348/143 |
| 6,323,773 B1 | * | 11/2001 | Runyon et al. ............. 340/573.1 |
| 6,760,233 B2 | * | 7/2004 | Tolle et al. ...................... 363/16 |
| 6,894,610 B2 | | 5/2005 | Schubert et al. |

(Continued)

FOREIGN PATENT DOCUMENTS

| EP | 0591585 | 4/1994 |
| EP | 0591585 A | 4/1994 |

(Continued)

*Primary Examiner* — George Bugg
*Assistant Examiner* — Sisay Yacob
(74) *Attorney, Agent, or Firm* — Hoyng Monegier LLP; Coraline J. Haitjema; David P. Owen

(57) ABSTRACT

A method is disclosed for monitoring personnel operating at a workplace within a confined space. The method involves providing a mobile workplace module comprising a video registration device producing video data, an audio interface for emitting and receiving audio data and a gas sensor to produce gas sensor data. The workplace module is mounted at least partially within the confined space and a mobile monitoring unit comprising a display for displaying video data from the workplace module, an audio interface for emitting and receiving audio data and a gas data receiver for receiving gas sensor data is located outside the confined space. The workplace module and the monitoring unit are connected by a mobile umbilical cable for data transmission so that personnel at the workplace may easily be monitored from the monitoring unit. Apparatus for carrying out the method is also disclosed including a mobile monitoring system, a workplace module, a video camera mount, an extractive gas detector and a computer system.

27 Claims, 11 Drawing Sheets

U.S. PATENT DOCUMENTS

| | | | |
|---|---|---|---|
| 7,158,026 B2 * | 1/2007 | Feldkamp et al. | 340/531 |
| 2001/0007530 A1 * | 7/2001 | Hosotani | 363/20 |
| 2002/0147982 A1 | 10/2002 | Naidoo et al. | |
| 2004/0137959 A1 * | 7/2004 | Salzhauer et al. | 455/567 |
| 2005/0043859 A1 * | 2/2005 | Tsai et al. | 700/286 |
| 2005/0049726 A1 * | 3/2005 | Adamson et al. | 700/19 |
| 2007/0229252 A1 * | 10/2007 | Collins et al. | 340/539.13 |
| 2007/0285222 A1 * | 12/2007 | Zadnikar | 340/509 |

FOREIGN PATENT DOCUMENTS

| | | |
|---|---|---|
| EP | 0869464 | 10/1998 |
| WO | WO95/01041 | 1/1995 |
| WO | WO97/36272 | 10/1997 |
| WO | WO99/16233 | 4/1999 |
| WO | WO 9916233 A2 * | 4/1999 |
| WO | 00/68908 A | 11/2000 |
| WO | WO00/68908 | 11/2000 |
| WO | WO02/19254 | 3/2002 |
| WO | 02/086834 A | 10/2002 |
| WO | WO02/086834 | 10/2002 |
| WO | WO02/093926 | 11/2002 |
| WO | WO01/58400 | 8/2007 |

* cited by examiner

SAFETY MONITORING SYSTEM

BACKGROUND OF THE INVENTION

1. Field of the Invention

The present invention relates to monitoring systems and devices and in particular to monitoring systems for use in the monitoring of workers operating in dangerous environments or under potentially dangerous conditions. The invention is especially applicable to the monitoring of personnel operating in confined spaces as are frequently encountered in the chemical, petrochemical and refining industries.

2. Description of the Related Art

In the following, reference will be made to the petrochemical industry and petrochemical plants. This is not intended to be limiting on the present application and in the present context is intended to include also chemical plants and refineries and all other locations where workers are required to work within confined spaces or under dangerous conditions where safety monitoring is required such as within boilers, tanks, tubing systems, ships holds or the like. Where reference is made to confined spaces, this term is generally understood in this context to refer to spaces which are not normally accessible and which are not usually intended as workplaces.

Petrochemical plants are generally designed to run around the clock with little or no day-to-day maintenance. At the end of a production run or as part of the long-term maintenance programme, the plant will be shut down and what is known in the industry as a "shutdown" or "turnaround" will take place. Such a turnaround will usually entail a thorough cleaning and complete overhaul of the plant. It is also an opportunity to upgrade the plant or redesign some aspects to improve efficiency or to adapt it for a different product or different working conditions. For some plants a turnaround may take place every 3 months; for other plants this may only take place once every three years or more. In all cases, the turnaround procedure is critical since the expense involved in keeping the plant inactive can amount to several millions of dollars per day.

For this reason, turnarounds are minutely planned well in advance, usually to coincide with a slack period in the yearly production cycle. These periods are usually spring and autumn, since summer is unsuitably hot for anything other than emergency work and for refineries, winter is usually the peak production season. During a turnaround, a huge contingent of personnel will descend on the plant. While many plants may function with less than 50 staff, a turnaround may involve up to 5000 people over e.g. a six-week period. These persons must be accommodated, entertained, supervised and supplied and the turnaround may operate 24 hours a day until the plant is recommissioned. In order to cope with the logistics of such events, specialised turnaround contractors are used, employing large numbers of temporary workers of varying skill levels.

Because of the nature of the environment, the work is potentially very dangerous. This factor, combined with the limited mental ability of certain workers and the time pressure under which the operation takes place result in the need for exceptional attention to all aspects of safety. To achieve this level of safety requires a yet further quantity of safety monitoring personnel. For work within a confined space, as is the case for personnel cleaning within a refinery column, a safety officer must be on duty for each person present within the column. The safety officer is required to remain immediately outside the access opening and continually monitor the work taking place within the column. In the event that any sort of emergency occurs, the safety officer is immediately available to intervene and commence the appropriate rescue procedure for the worker or workers within the column. Most of the time however, the safety officers only intermittently observe. Such inactivity leads to boredom and frequently they may become distracted, lose concentration and even fall asleep or go off for a coffee. A major problem with work in such environments is the lack of continuous attention to safety and a tendency by both workers and "safety" officers to cut-corners wherever possible or shirk responsibility. Even when the safety officers act conscientiously, since much of the work takes place out of sight within the confined space, rigorous observation of the work is difficult or incomplete.

Under certain circumstances, workers may be required to work within a sealed environment. This may be the case where the levels of noxious gas are so high that the area must be sealed completely. Such situations may occur when breaking up benzine columns where a hermetically sealed tent is erected over the complete structure. It can also occur that the contents of the plant e.g. a catalytic column are unstable in air. In such circumstances, it may be necessary to operate in an environment of nitrogen. In both of these examples the workers are required to operate with breathing equipment. Clearly, it is impossible for the safety officer to effectively monitor without entering the sealed environment and being exposed to the danger himself.

In assuring the safety of operating personnel, the safety officer may also be required to monitor the identity and/or qualification of the personnel. This may frequently be achieved simply by knowledge of the individuals and the nature of the different operations that they are authorised to conduct. Under situations where many individuals, in particular temporary and contract staff, are employed, such checks may be conducted by the use of authorisation certificates and identity cards. In this way, only an authorised and competent person may be permitted to conduct a particular operation, e.g. welding using oxy-acetylene within a given environment such as a fractionating column.

An additional function of the safety officers may be the periodic measurement of the air composition at the workplace. This may involve the introduction of a hand held gas analyser through the access man-hole into the column interior and reading out the result. If the gas analyser gives a reading indicating that noxious or flammable gases are present, the safety officer is required to immediately alert and evacuate any personnel present within the column. Periodic measurement of the air composition at the access opening does not always provide a reliable indication of the actual condition under which the personnel are working. In addition to possible risks of explosion, many of the gases encountered are potentially dangerous, especially in large doses. At present it has been customary to carry out urine tests on workers at the end of every shift in order to determine levels of exposure to particular chemicals. If excess levels are encountered in the urine, the worker may be barred from working during the following shift.

In addition to safety monitoring of the workplace, it is essential that periodic inspection of the work takes place to assure that it is correctly and safely executed. Inspection may be carried out by the safety officers or other members of the contracting team. Additionally or instead, it may be carried out by personnel from the refinery or plant in order to guarantee the quality of the work. Such inspections are however difficult to achieve when the work proceeds at a high rate. Frequently, sections of the plant will have been reassembled prior to an inspection taking place. In the case of refinery fractionating columns, such columns are built up from large numbers of layers of dishes. Once a layer has been completed it is no longer possible to determine whether the layer below has been correctly assembled.

There is thus a need for a system whereby adequate monitoring of a workplace, in particular a confined space, can be achieved while fulfilling all reasonable requirements of safety and also allowing for inspection of the work at all stages of its completion. At present, no system is available which meets these stringent requirements.

In the field of security systems, in particular building and site security systems, it is well known to provide video monitoring equipment whereby a security officer at a central location can monitor various remote locations around the building. Such systems may employ a number of video cameras which feed back images to the central location where they can be viewed on an appropriate video screen or on a number of video screens. A device employing video cameras for building security is known from U.S. Pat. No. 5,382,943. Such devices are intended to provide a level of visual security sufficient for e.g. prevention against robbery or detection of intruders. They may also be provided with a gas sensor for the purpose of fire detection. Such systems are however designed to be permanently integrated into a building environment and are not adapted for mobile deployment at a workplace. In particular, the use of radio transmission between the video camera and monitor is unsuitable for use in the context of refinery fractionating columns where transmission is impeded by the steel wall of the column. Furthermore, they are generally of a construction and configuration which makes them unsuitable for use in a workplace.

Various alternative systems have also been suggested utilising two way video and audio links, allowing an individual at a central location to communicate with an individual at a remote location and vice-versa. Such devices may be used in providing guidance for the performance of complicated procedures such as the servicing of machines. A system for instructing personnel in the operation of machinery at a plant is known from U.S. Pat. No. 5,844,601. This system is neither contemplated nor adapted for ensuring the safety of the operating personnel.

BRIEF SUMMARY OF THE INVENTION

According to the present invention there is provided a method of monitoring personnel operating at a workplace within a confined space, the method comprising: providing a mobile workplace module comprising a video registration device producing video data, an audio interface for emitting and receiving audio data and a gas sensor producing gas sensor data; mounting the workplace module at least partially within the confined space; providing a mobile monitoring unit outside the confined space, the monitoring unit comprising a display displaying video data from the workplace module, an audio interface for emitting and receiving audio data and a gas data monitor for receiving gas sensor data; connecting the workplace module to the monitoring unit for data transmission therebetween; and monitoring at the monitoring unit the operation of personnel at the workplace. In this way, a safety officer present at the monitoring unit can closely follow the work at the workplace without being exposed to the dangers associated with the confined space.

According to a preferred embodiment of the invention, the method further comprises detecting the presence or identity of personnel at the workplace. This information may then be made available to the safety officer e.g. on the display or on a separate data screen, whereby it can easily be determined who is present at the workplace at any particular time and what the nature of their work should be.

Preferably, the gas sensor data is compared with predefined limits and a warning is provided if these limits are exceeded. The warning may be given audibly both to the safety officer at the monitoring unit and to the personnel working at the relevant workplace. It may also be provided on the display or may be provided on a separate data screen. The gas sensor may be located directly at the workplace or may be an extractive gas detector located remotely outside the workplace. A number of gas sensors may also be used, both local and remote.

According to an important aspect of the present invention, a number of workplaces may be monitored from a single monitoring unit by providing further workplace modules at the further workplaces. The invention further includes a computer system incorporating a software module, which allows a safety officer to easily and efficiently access relevant data related to each of the workplaces under his or her control. The computer system comprises a monitor, a processing unit, and a plurality of video and gas data inputs associated with individual workplaces, the processing unit being programmed to compare the gas data inputs with predetermined reference values and cause display on the monitor of gas data which exceeds the reference values together with further data related to the workplace associated with the displayed gas data. The computer system may be easily configurable to add on or remove further workplace modules and to reconfigure workplace modules having different components.

According to the present invention, there is also provided a safety monitoring system for monitoring of a workplace within a confined space, comprising: a mobile workplace module comprising a video registration device producing video data, an audio interface for emitting and receiving audio data and a gas sensor producing gas sensor data; and a mobile monitoring unit selectively connectable to the workplace module for data transmission between the workplace module and the monitoring unit, the monitoring unit comprising a display displaying video data from the workplace module, an audio interface for emitting and receiving audio data and a gas data monitor for the gas sensor data.

Advantageously, the safety monitoring system further comprises a presence detector, which may be in the form of a registration device for registering the entry and exit of personnel into the workplace. The presence detector may provide identification data concerning the detected personnel to the monitoring unit for display on the display or on a separate data screen. Further data concerning the identified personnel may be provided to the monitoring unit or data screen from other sources such as a central personnel database or a work-planning database.

According to a preferred embodiment, the monitoring unit comprises a recording device for producing and maintaining a record of selected data. Preferably, the data is recorded in digital form whereby compression and sampling techniques can be used to minimise the volume of data recorded. Such a record can be extremely useful as a "black box" for reviewing certain events e.g. in the event of an incident, or for checking on the correct completion of the work.

According to an important aspect of the present invention, the safety monitoring system may comprise a number of workplace modules. Each workplace module may be conveniently and selectively connected to the monitoring unit using a single umbilical carrying all necessary data. Preferably, the umbilical uses optical fibres to reduce signal distortion during transmission. According to an additional feature of the invention, each workplace module is easily configurable to comprise a number of video cameras, gas sensors or registration devices and is provided with additional input capacity for further optional components.

Because gas detection of a large number of gases can require bulky equipment including a number of expensive detector heads, it is particularly convenient to locate such devices outside the workplace. According to a further aspect of the present invention there is provided a method of monitoring gas at a plurality of workplaces comprising providing an extractive gas detector having a plurality of gas detection heads and a plurality of supply conduits; locating free ends of the supply conduits at the plurality of workplaces extracting gas from each of the workplaces; and periodically supplying the extracted gas to selected gas detection heads.

BRIEF DESCRIPTION OF THE DRAWINGS

Embodiments of the present invention will now be described, by way of example only, having reference to the accompanying figures, in which.

DESCRIPTION OF ILLUSTRATIVE EMBODIMENTS

Figure 1:
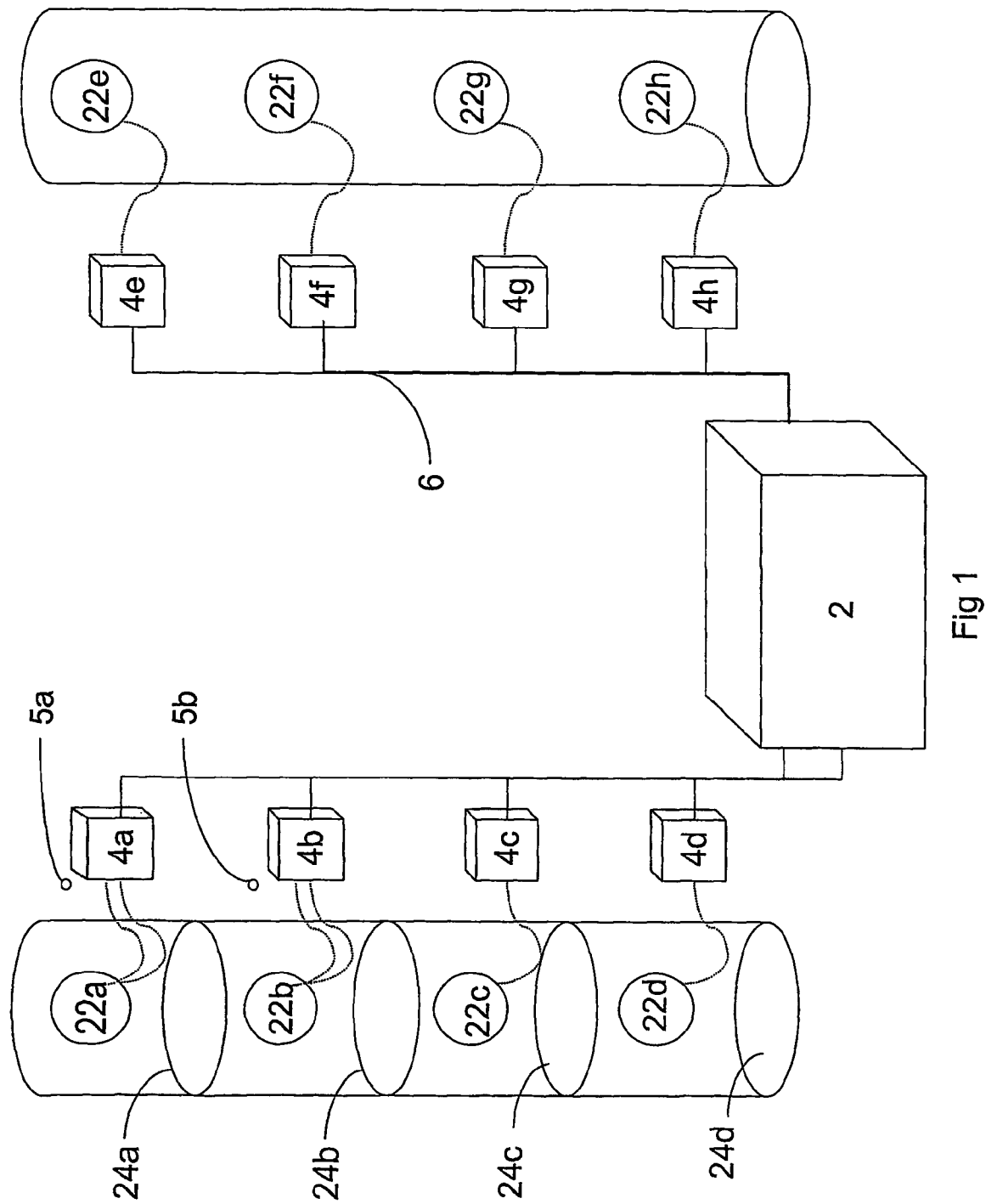
FIG. 1 is a schematic overview of a safety monitoring system according to the present invention.

FIG. 1 shows a schematic overview of a safety monitoring system 1 according to the present invention. The safety monitoring system 1 as shown in FIG. 1 includes a mobile monitoring unit 2 and a number of workplace units 4, connected together via an umbilical 6.

The monitoring unit 2 is preferably a container or Portokabin™ type accommodation which can be easily relocated at the site where work is being carried out—in the present case, at a petrochemical plant in the vicinity of two fractionating columns 20, 21. In the present context, this is intended to denote that the monitoring unit 2 is within immediate walking distance of the columns 20, 21 such that, in the event that intervention is required, a safety officer at the monitoring unit 2 can immediately assist personnel operating within the columns 20, 21. It is, however, also within the scope of the present invention that the monitoring unit is located remotely from the workplace units, with communication being provided by satellite, telephone, internet or the like. In such an arrangement, a local safety officer may be provided at the plant in the immediate vicinity of the columns 20, 21.

The workplace units 4a-h are each located adjacent to one of the manhole openings 22a-h in the fractionating columns 20, 21. The manhole openings 22a-h provide access to workplaces 24a-h located within the columns 20, 21. In the illustrated embodiment, the workplace units 4 are all identical. The workplace units 4 are provided with monitoring components to form a workplace module 5a-h. In practice, each workplace module 5 may comprise different components according to the requirements of the individual workplace. They may also share, or partially share, certain components, as will be explained in further detail below.

The umbilical 6 provides the data transmission between the workplace units 4 and the monitoring unit 2. In the present context, data is intended to include all types of data including both digital data and analogue data. Umbilical 6 comprises a number of fibre-optic cables and conventional data cables bundled together and provided with appropriate external protection. The use of optical cables has been found extremely advantageous in ensuring interference-free data transport within such an environment. During a turnaround at a petrochemical plant, the nature of the work being carried out, in particular welding and cutting, can produce substantial electromagnetic interference. This work is mainly carried out on the ground between the columns 20, 21 and the monitoring unit 2 and the interference is mainly of relatively short range. Conventional electrical data cables traversing the route between the columns 20, 21 and the monitoring unit 2 have been found to be affected by such interference whereby certain signals are severely disrupted. As will be described below, conventional data cables may be used at other locations within the safety monitoring system 1 less subject to interference. Alternatively, optical cables may be used throughout. The present invention is not considered limited to the use of an umbilical of cables from all workplace units. Each workplace unit 4 may be provided with its own independent connection to the monitoring unit. Furthermore, the connection between the monitoring unit 2 and the workplace units 4 may be provided by a wire or cable connection, a wireless connection or any combination of the above depending upon the specific environment encountered. In the case that the monitoring unit 2 is located at a remote location, an umbilical 6 may be used to connect the workplace units 4a-h to a transmitting station from which the signals may be transmitted to the remote location e.g. by a satellite link.

Figure 2:
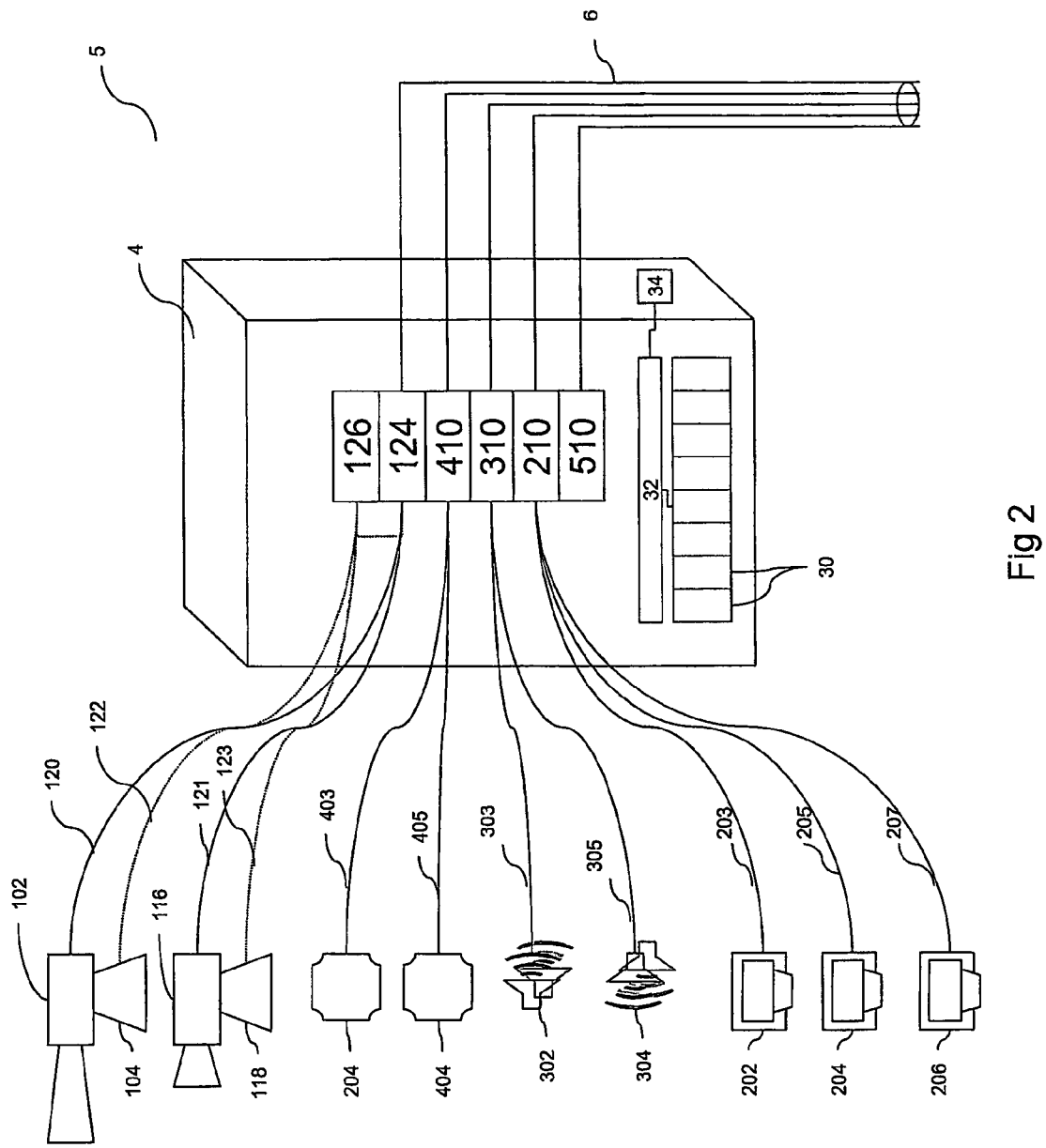
FIG. 2 is a schematic representation of a workplace module.
Figure 3:
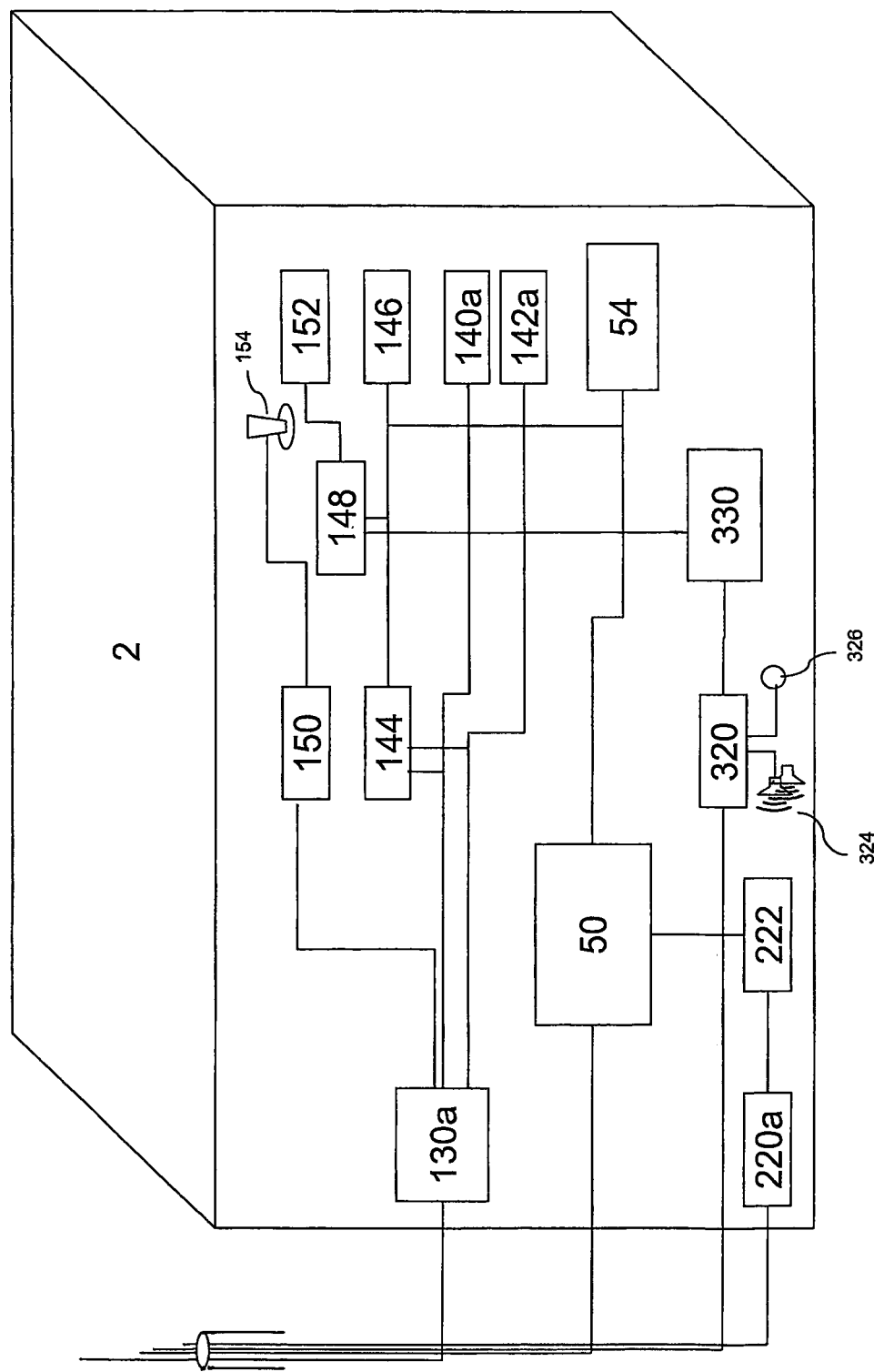
FIG. 3 is a schematic representation of a monitoring unit according to the present invention.

FIGS. 2 and 3 illustrate the safety monitoring system 1 in greater detail. For the sake of clarity, only a single workplace module 5 is depicted. The safety monitoring system 1 is made up of a number of subsystems each of which will be described individually below. It is believed that each of the subsystems is itself and in the context in which it operates, new and inventive. Each subsystem is embodied partially within the monitoring unit 2 and partially within the workplace modules 5. Within the monitoring unit 2, the subsystems may be incorporated as software programs running on a computer in combination with hardware such as video monitors 54, 140, 142, 146 and audio speaker 324. Within the workplace module 5, the subsystems may be embodied as hardware elements such as video cameras 102, 116 and gas detectors 202, 204, 206. These components may be provided with further local software where necessary. Certain components may also be shared by more than one subsystem.

FIGS. 2 and 3 show the integration into the monitoring unit 2 and a workplace module 5 of a video monitoring subsystem 100 by which video images of the workplace are received and viewed, a gas sensor subsystem 200 by which individual gases may be detected and analysed; an audio communication subsystem 300 for 2-way audio communication with the workplace and an access registration subsystem 400 for monitoring and registering access to the workplace. Optional subsystems 500 may also be provided for specific circumstances.

The Video Monitoring Subsystem

The video monitoring subsystem 100 will be described in further detail with reference to FIGS. 2 to 4. The video monitoring subsystem 100 comprises a video camera 102 mounted within the column 20 for tilting and panning motion on motor unit 104. Such a video camera is well known in the art and will not be described in further detail. It has been found particularly important that the video camera should be capable of zooming in to great detail, in order to be able to follow the precise actions being performed by individual workers present at the workplace. This is particularly important for maintaining an accurate record of the full sequence of actions performed, which may be checked later in the event of discrepancy. It has also been found that high definition video cameras with mechanical zoom and mechanical movement are highly suited to this function. Fixed digital cameras may also be used, where the zooming, panning and tilting is achieved by digital enhancement of the image. At present, the definition provided by such devices has been found insufficient, although a mechanical zoom followed by digital enhancement is nevertheless favoured.

Figure 4:
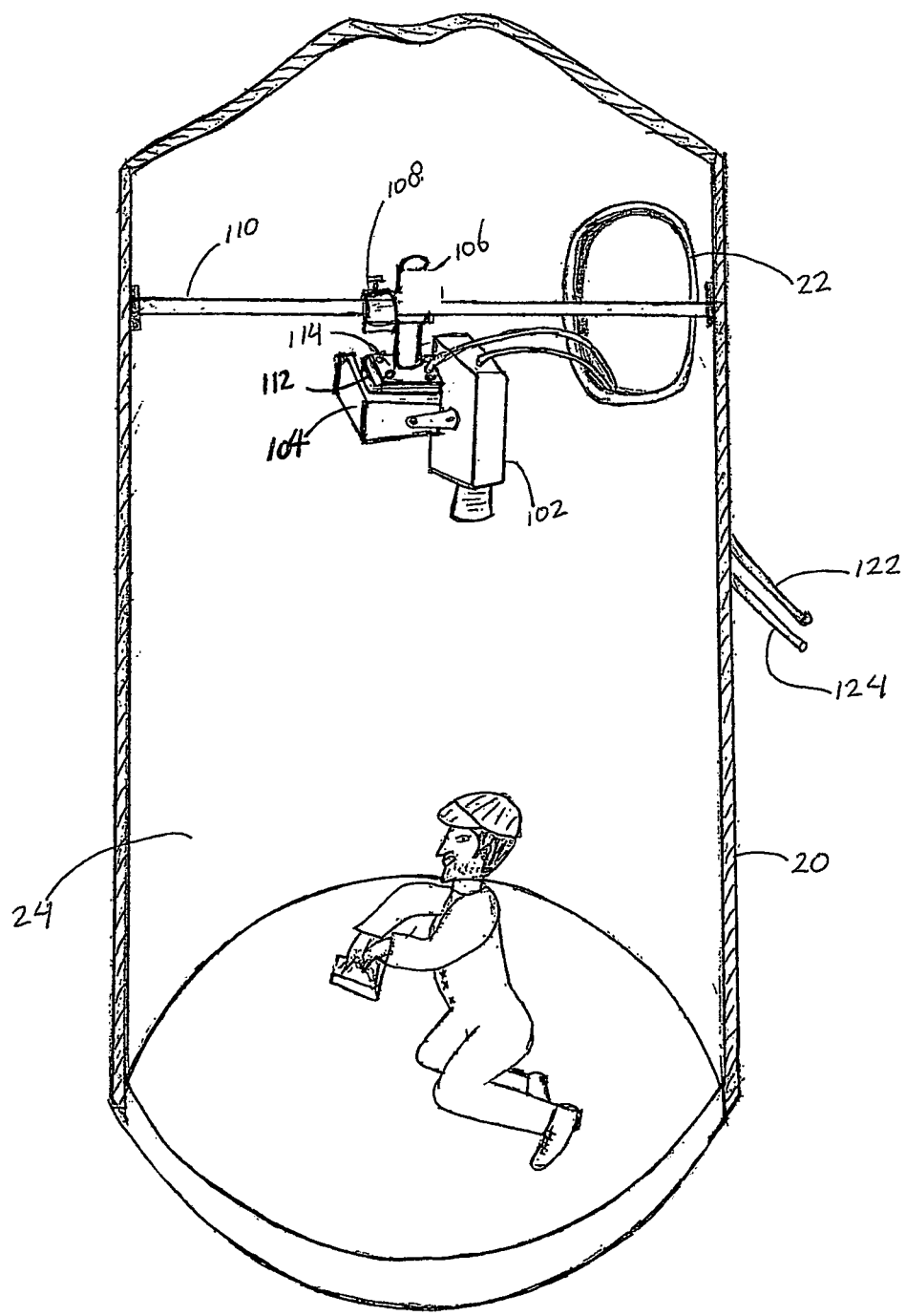
FIG. 4 is a perspective view of a video camera mounted within a petrochemical column according to a further aspect of the present invention.

FIG. 4 shows in further detail the mounting of video camera 102 within the column 20. In order to assure that the detail required and achievable from the video camera 102 is actually realised, the video camera 102 must be securely mounted to reduce or remove vibration or undesired movement, particularly during operation of the motor 104. Secure mounting of such a large and sensitive item is in general difficult. In the context of a temporary installation within, e.g. a fractionating column or industrial boiler, this is particularly difficult as it is in general unacceptable to bolt the camera to a wall of such an installation. To overcome this problem in accordance with the present invention, it has been found that by providing the video camera 102 and motor 104 with a mount 106 having the external cross-section of a standard scaffold pole, the video camera 102 may be firmly clamped with a standard scaffold clamp 108 to a scaffold pole 110 or other element of scaffolding used within the installation. The mount 106 may thus have a round cross section of external diameter of between 4.5 cm and 5.5 cm, preferably between 4.9 cm and 5.1 cm. The mount 106 may be formed of steel or aluminium alloy depending upon the type of scaffold with which it is intended to match. Video cameras 102 are usually provided with a flange mounting 112. According to one aspect of the present invention mount 106 comprises a corresponding flange 114 which may be connected to flange mounting 112 by bolting, welding or other standard fastening procedures. Where different scaffold sizes are encountered, it may also be possible to provide mounts 106 of different diameters or cross-sections each provided with a flange 114 for interchangeable connection to the flange mounting 112.

For installation of the video monitoring subsystem 100 for use within fractionating column 20, a scaffold pole 110 having a length corresponding substantially to the interior diameter of the column 20 is inserted diagonally across the column via a manhole opening 22. Expander members (not shown), well known in the industry, are used to lengthen the scaffold pole 110 sufficiently to lock it firmly in place across the column. Thereafter, the video camera 102 may be firmly attached by mount 106 to the scaffold pole 110 using scaffold clamp 108.

For normal operation it has been found sufficient to provide a spatially fixed mounting for the video camera 102, reliance being made on zoom, pan and tilt (either digitally or mechanically) to adequately follow the subject. Under certain circumstances such as in elongate columns with only a single access, it may be desirable to provide a mobile mount for the camera whereby it can be moved to follow the work taking place. In such circumstances it may be desirable to provide a track along which the camera may ride. Such a track could be mounted e.g. vertically within the column. By following the work more closely it may be possible to use video cameras of lower specification or to thereby alleviate the need for further mechanical zoom. According to a yet further alternative, the video camera 102 may be mounted in a completely mobile fashion, e.g. on the body or helmet of one of the workers operating at the workplace. If a head mounted video camera is used, it may be desirable to use a local wireless connection for data transfer between the camera and a receiver located at a fixed point within the column. A video data cable may then be employed to transmit the signal to the exterior of the column.

Video monitoring system 100 also comprises a second video camera 116. The second video camera is mounted outside the column 20 to provide an overview of the immediate vicinity of the manhole opening 22a. Preferably, the second video camera is mounted to also provide an image of the workplace unit 4 such that the correct placement and use of this unit can also be monitored by the safety officer from the monitoring unit 2. The second video camera is a fixed lens camera mounted on a motor unit 118 for panning and tilting motion. Although the second video camera is a fixed-lens camera, digital picture enhancement or the like is nevertheless possible to provide further detail where necessary. It is also possible to omit the motor unit 118 and rely on enhancement of a wide-angle image.

Video cameras 102, 116 are connected by video data cables 120, 121 to a video transmitter 124 in the workplace unit 4 for transmission of video data. The video transmitter 124 is a fibre-optic modem, which converts incoming electrical signals into optical signals for transmission via umbilical 6 to the monitoring unit 2 and vice-versa. Motor units 104, 118 are connected via control cables 122, 123 to a control unit 126 within the workplace unit. Control unit 126 is also connected to the video transmitter 124. Control data for controlling movement of the video cameras 102, 116 may thus also be transmitted over the same fibre together with the video data. Power cables (not shown) are also connected to power out sockets 30 on the workplace unit 4 for providing low voltage power to the video cameras 102, 116 and the motor units 104, 118. The power out sockets 30 are fed with power from a low voltage isolation transformer 32 provided in the workplace unit 4. For work in such environments, a safe voltage supply of 24V is provided to the power out sockets 30. Other voltages may also be used depending upon the environment and the local regulations. Alternatively, different voltages may be provided to different power out sockets 30. Power to the transformer 32 is supplied via power in socket 34 from a standard electrical supply local to the column 20.

A video receiver 130a is provided in the monitoring unit 2 (see FIG. 3). In the following, reference numerals followed by a letter will be used to denote components of the monitoring unit 2, which are duplicated for each workplace module 5a-h or workplace unit 4a-h present in the system. Components denoted without such a letter are understood in the present example to be present as single items. Video receiver 130a is also a fibre-optic modem and serves to convert incoming optical signals from the umbilical 6 into electrical signals for further processing within the monitoring unit 2. Although only one video receiver is shown in FIG. 3, the monitoring unit 2 is provided with a bank of eight (or more) such devices for receiving video and control data from each workplace unit 4. The video receiver also splits the signal into an incoming analogue video signal and an outgoing control data signal.

The video signal is provided to video monitors 140*a* and 142*a*, which continuously display an analogue image from video cameras 102 and 116 respectively. It has been found that analogue video images are superior to digitally produced images for the purpose of monitoring. This is particularly the case when the image is zoomed. The video signal is also provided to a video converter 144 which converts the incoming analogue signals to digital video signals and provides them as images to a digital multiplex monitor 146 and a digital video recorder 148. Manipulation of these images will be described in further detail below.

The control data signal is provided by a camera controller 150, which receives inputs from a joystick unit 154 by which the safety officer may control the operation of the different cameras throughout the safety monitoring system 1. The joystick unit 154 is provided with a number of keys whereby an individual video camera may be addressed. Operation of the joystick then allows movement and, where possible, zooming of the addressed video camera. The monitors 140*a* or 142*a* and 146 display the resulting image.

The digital video recorder 148 is connected to a keyboard 152. Other controlling devices such as a mouse or joystick may also be provided. The keyboard allows control of the recorded images and their playback on multiplex monitor 146. It may also be used to rearrange the individual workplace images within the multiplex monitor to any desired configuration.

The video monitoring subsystem 100 also comprises a video software module, which will be described in more detail below in conjunction with the operation of the data monitor 54 and the other subsystems.

The Gas Sensor Subsystem

The gas sensor subsystem 200 will be described in further detail with reference to FIGS. 2 and 3. Workplace module 5 comprises a number of local gas detector heads 202, 204, 206 suspended by their cables 203, 205, 207 within the column 20. Each detector head is dedicated to the detection of a particular gas or composition. In the present example detector head 202 is for detecting oxygen, detector head 204 monitors the so-called lower explosive level (e.g. the ratio of pentane to oxygen) and detector head 206 detects the presence of hydrogen sulphide. Other detector heads may be used instead or in addition according to the safety requirements of the particular column. The location of the detector heads within the column will be determined by the nature of the gas to be detected, thus heavier gases such as CO may require the detector head to be suspended close to the workfloor while lighter gases, which may nevertheless constitute a danger of explosion, may be better detected at a higher level within the column 20. The detector heads 202, 204, 206 are each linked by their cables 203, 205, 207 to the workplace unit 4 and provide gas data to a gas transmitter 210. They also receive electrical power by connection to a power-out socket 30.

The gas transmitter 210 is also in the form of a fibre-optic modem which converts the incoming gas sensor data from all three detector heads 202, 204, 206 into an optical signal on an optical fibre for transmission via the umbilical 6 to the monitoring module 2. Within the monitoring unit 2, the optical fibre connects to a gas receiver 220*a* in the form of a fibre-optic modem, which reconverts the optical signal into an analogue signal and passes it on to a modbus interface 222. Modbus interface 222 serves to bring all the signals together from different gas receivers 220*a-h* and converts the signals into a digital input to a central processor unit 50 operating under TCP/IP (Transmission Control Protocol/Internet Protocol). The CPU 50 supplies data on demand to data monitor 54 as will be described below in relation to the software module. The CPU 50 may be programmed with appropriate reference and limiting values for the individual gases. If the limits are exceeded, an appropriate alarm will be given to warn the safety officer.

Figure 5:
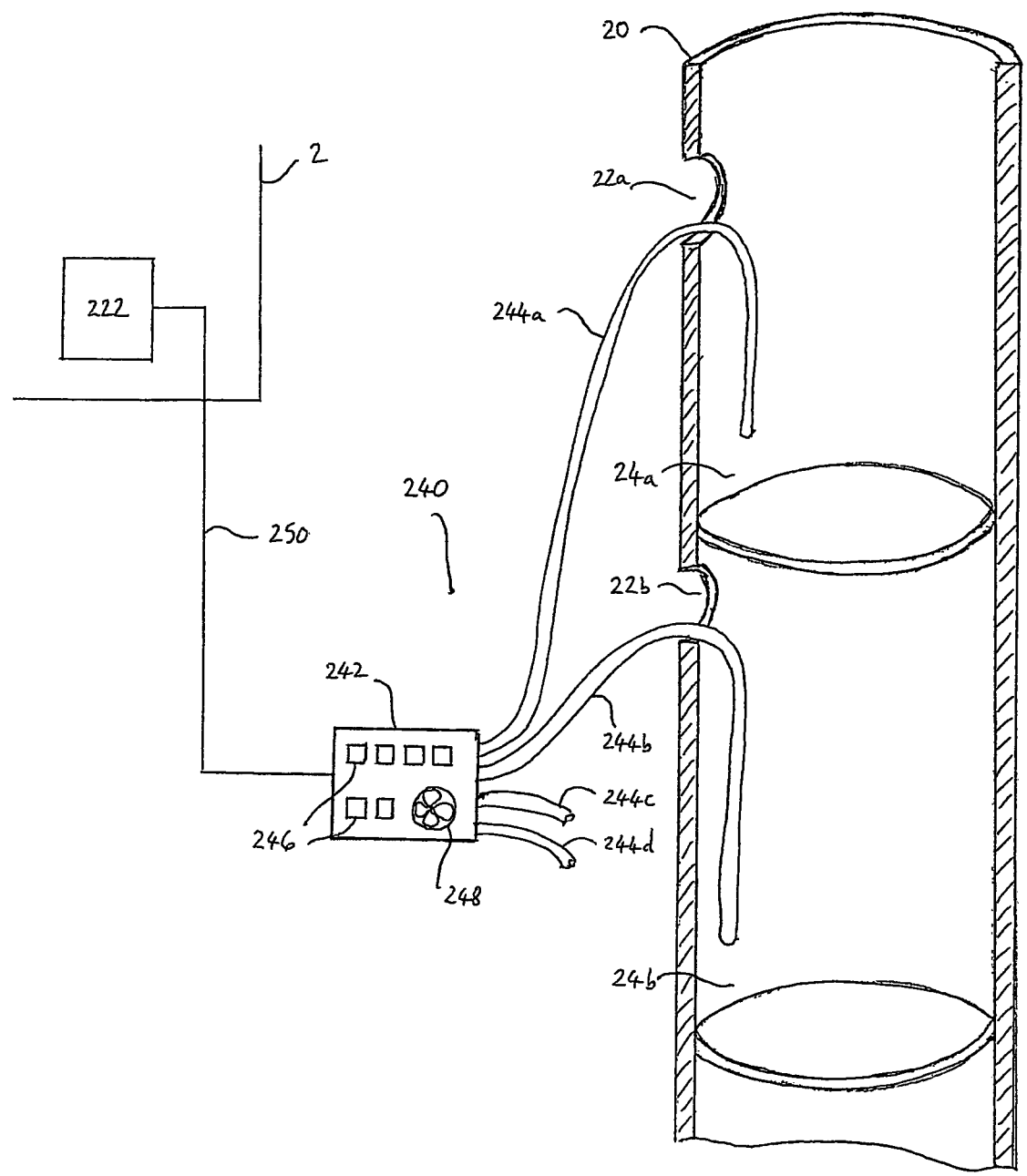
FIG. 5 is schematic view of an extractive gas sensor according to another aspect of the present invention.

An additional or alternative component of the gas sensor subsystem 200 is shown in FIG. 5. Other items of the safety monitoring system 1 have been omitted for the sake of clarity. According to FIG. 5, gas sensor subsystem 200 may also include an extractive gas module 240 comprising an extractive gas detector 242. Such extractive gas detectors are generally known for the purpose of providing permanent gas detection within fixed installations. It is believed that the use of such a device for temporary monitoring of the atmosphere at a workplace within a confined space as described below is in itself inventive. Such an extractive gas module may thus be used as a stand-alone device for workplace monitoring of confined spaces or may be used in combination with other monitoring subsystems. If used as a stand-alone device, it may be provided with its own display means.

The extractive gas detector 242 is provided with a number of hose connections 244*a-d*. Hose connection 244*a* extends into the column 20 via manhole opening 22*a* and terminates at the workplace 24*a* at a distance of about 1 m above the workfloor. This position for gas extraction may be subject to local laws and requirements. A second hose connection 244*b* extends into column 20 via manhole opening 22*b* and terminates at the workplace 24*b*. Further hose connections 244*c* and 244*d* may extend to the other workplaces within column 20. Alternatively, hose connections 244*c* and 244*d* may also be used for additional monitoring of the workplaces 24*a* and 24*b*.

The extractive gas detector 242 includes a number of gas detector heads 246. Each gas detector head 246 is capable of analysing a single gas and the extractive gas detector 242 may be configured with different gas detector heads 246 depending upon the gases, which it is required to monitor. The extractive gas detector 242 is also provided with an aspirating device 248 in the form of a fan or pump.

In use, the aspirating device 248 operates to extract air (or other gas) from the workplaces via the hose connections 244*a-d*. The air is fed to the detector heads 246 where the presence of selected gases in the air is measured. The extractive gas detector is also provided with exchange means (not shown) which allows the air from any particular hose connection 244*a-d* to be directed to any one of the detector heads 246. The sampling of air from different sources for the presence of different gases may be automated or may be directed by the safety officer.

Extractive gas detection signals from the extractive gas detector 242 are transmitted via a data cable 250 for monitoring. In the embodiment according to FIG. 5, the extractive gas detection signals are fed via cable 250 to the modbus interface 222, where they are further processed in much the same way as the signals from the local gas detector heads 202, 204, 206. If the signal from the extractive gas detector 242 must pass through an area of high interference, a fibre-optic modem and optical fibre link may be used. In this case, the monitoring unit 2 may be provided with an additional gas receiver (not shown) in parallel with gas receivers 220*a-h* for receiving the incoming signal from the extractive gas detector 242.

By providing an' extractive gas detector with a number of heads serving a number of different workplaces, a more economical use of resources is achieved. Although the illustrated embodiment operates with four hose connections, many more connections are possible, and a single extractive gas detector may provide sufficient gas detection for a monitoring unit monitoring e.g. eight workplaces without the further requirement of local gas detector heads.

The Audio Communication Subsystem

The audio communication subsystem 300 is also depicted in FIGS. 2 and 3. It comprises a microphone 302 and an audio speaker 304 located within column 20 in an appropriate position to allow clear and convenient two-way communication with personnel operating at the workplace 24. Microphone 302 and speaker 304 are linked to the workplace unit 4 by cables 303, 305, which may be standard data cables.

The workplace unit 304 comprises an audio interface 310, which provides for the necessary amplification of the audio signals to and from the workplace 24. The audio signals are transmitted as analogue signals via conventional audio standard cables through the umbilical 6 to the monitoring unit 2. It has been found that in the context of workplace monitoring, full duplex analogue audio communication via a dedicated cable ensures the best results.

Within the monitoring unit, as can be seen in FIG. 3, the audio signal is provided to a central audio interface 320. Central audio interface 320 receives audio signals from and supplies audio signals to all workplace modules 5 and is also connected to monitoring unit speaker 324 and monitoring unit microphone 326 for communication with the safety officer present within the monitoring unit 2. The central audio interface 320 is provided with its own dedicated hardware switching (not shown) to selectively control operation of the various speakers 304$a$-$h$, 324 and microphones 302$a$-$h$, 326. The safety officer may thus listen to all the microphones 304$a$-$h$ together or may select an individual microphone e.g. 304$c$ to monitor in detail. Similarly, he may address all the workplaces together via microphone 326 and speakers 304$a$-$h$ or he may selectively address one individual workplace or a group of workplaces e.g. the workplaces 24$e$-$h$ in column 21.

The separate audio interfaces 310$a$-$h$, 320 and independent transmission via umbilical 6 as well as the dedicated hardware switching ensures independence of the audio communication system 300 from the other subsystems. For safety reasons, this independence permits continued contact between the workplaces 24$a$-$h$ and the monitoring unit 2 even if faults develop elsewhere. The central audio interface 320 also supplies signals to a digital converter 330, which continuously converts the audio signals to a digital audio data stream and transmits this for recording by digital video recorder 148.

The Access Registration Subsystem

An important feature of the present invention is the provision of immediate up to date data to the safety officer concerning which persons are located at which locations and what duties are assigned to them. This is particularly important in assessing the safety of a particular situation and also in accounting for personnel in the case of an accident. Access registration subsystem 400 comprises a pair of magnetic card readers 402, 404. Card readers 402, 404 are generally conventional card reading devices, capable of recognising a magnetic card placed close to the reader. Card reader 402 is designated as the entry card reader and is attached to the column 20 adjacent to the manhole opening 22$a$. Workers operating at the plant are all provided with identity cards giving access to certain information about the individual worker and including their work assignment. On entry to the column via manhole opening 22$a$, a worker will present his card for recognition by the entry card reader 402. Card reader 404 is designated as an exit card reader and is located on the workplace unit itself. On exit from the column, a worker must again present his card to the exit card reader 404. Data cables 403, 405 link the card readers to a registration data transmitter 410 located within the workplace module 4. Registration data transmitter 410 is a fibre-optic modem, which converts electrical signals from the card readers 402, 404 to optical signals in one of the optical fibres of the umbilical 6.

The monitoring unit 2 receives the incoming registration data signals in the form of TCP/IP data directly at the CPU 50, which is provided with fibre-optic modems for this purpose. The CPU in turn provides this registration data on demand to the data monitor 54 as will be described further below. It should be noted that under certain circumstances, a person may enter a workplace, e.g. column 20 through a first manhole opening e.g. 22$a$ and may exit through another manhole opening e.g. 22$d$ if internal partitions have been removed during the work. The CPU 50 is programmed to acknowledge entry and exit of workers via different routes and to provide the necessary notification to the safety officer via data screen 54.

Although the presently described embodiment makes use of two card-reading devices located externally of the column, a single card reader for both ingoing and outcoming personnel may also be used. Other alternative or additional devices and methods for access control and recognition may also be provided. In a preferred embodiment, the card reader may be provided around the manhole opening so that a worker entering the confined space will automatically be registered. Alternatively, an identification device such as a card reader, iris recognition system or otherwise may be combined with a detection device whereby a person entering the confined space will generate an alarm if correct identification has not already taken place. Detection may take place by many methods including video image analysis, infrared or other temperature sensors, light beams and proximity sensors. The detection of a person entering the workplace may also be used to activate some or all of the other subsystems.

In a particularly advantageous embodiment, the access registration system may be arranged to detect absence rather than presence. While this is not directly access registration, it will be dealt with in the context of this subsystem. The video monitoring subsystem may be arranged to analyse the video image produced by either of the video cameras 102, 116 for the presence of motion or other changes in the image. If motion is detected, a signal may be given, e.g. to the safety officer or to processing unit 602 described below, for monitoring to commence. Of greater significance however is that the video image may be analysed to detect a lack of movement. Thus, if there is a lack of movement detected for more than one minute, the safety officer may be alerted. This may simply be due to movement of the worker out of the field of vision. If this is the case, the safety officer may redirect the video camera. For other situations, the safety officer may investigate further e.g. by use of the audio communication subsystem 300. A similar result may be achieved by analysis of audio data from the workplace to detect the presence or absence of characteristic sounds.

Optional Subsystems

The workplace units 4 are provided with an additional fibre-optic modem 510 connected to a vacant optical fibre of the umbilical. Fibre-optic modem 510 may be connected to additional measuring equipment in or around the column 20 according to requirements. Such additional measuring equipment could include: sound level measuring devices for registering both the immediate and the long-term exposure to high sound levels; breathing supply monitoring, for monitoring the correct supply of air to personnel working with breathing apparatus; heart beat monitors for measuring the state of activity or condition of the personnel; temperature measuring devices for monitoring the workplace temperature etc. Such additional measuring equipment will be provided with corresponding monitoring equipment located within the monitoring unit.

The Software Interface

FIGS. 6 to 10 illustrate in detail the operation of the software interface 600 provided by the data monitor 54. The data monitor 54 comprises a processing unit 602, which is loaded with software including graphics programs and associated drivers for producing a series of interactive displays on data monitor 54. The ease and convenience with which essential safety related information can be made available to the safety officer of vital importance, in particular in life and death situations. Although the present software interface 600 is described in conjunction with the earlier described subsystems 100-500, it will be understood that it is independent of the precise nature of the hardware components contained in those subsystems. The processing unit 602 may also be loaded with data concerning various data limits such as the gas alarm limits described in conjunction with the gas sensor subsystem above.

Figure 6:
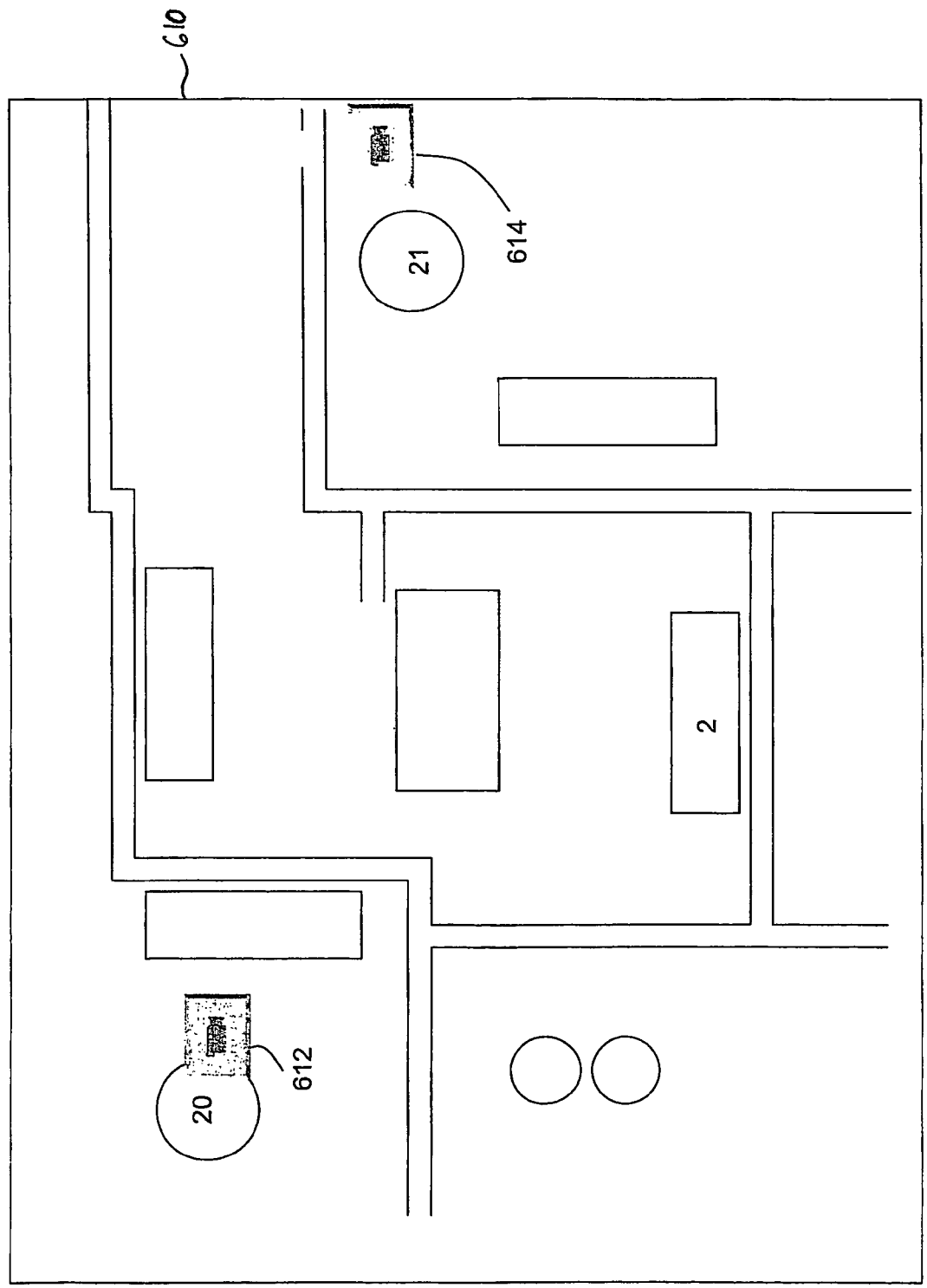
FIGS. 6 to 10 are display screens representing operation of the software module according to a yet further aspect of the present invention.

FIG. 6 shows the primary screen 610 available via the software interface 600 on data monitor 54. Primary screen 610 provides an overview of the plant or site indicating the location of important objects such as access roads, hazardous products, emergency services etc. Such information is prepared and input into the processing unit 602 during preparation for the turnaround. It also indicates the location of the columns 20, 21 being monitored and of the monitoring unit 2. The data monitor is a touch screen device and the software interface is configured to respond to actuation of various areas of the screen. In primary screen 610, camera icons 612, 614 indicate the currently monitored locations and are also configured as touch areas as will be described in further detail below.

Figure 7:
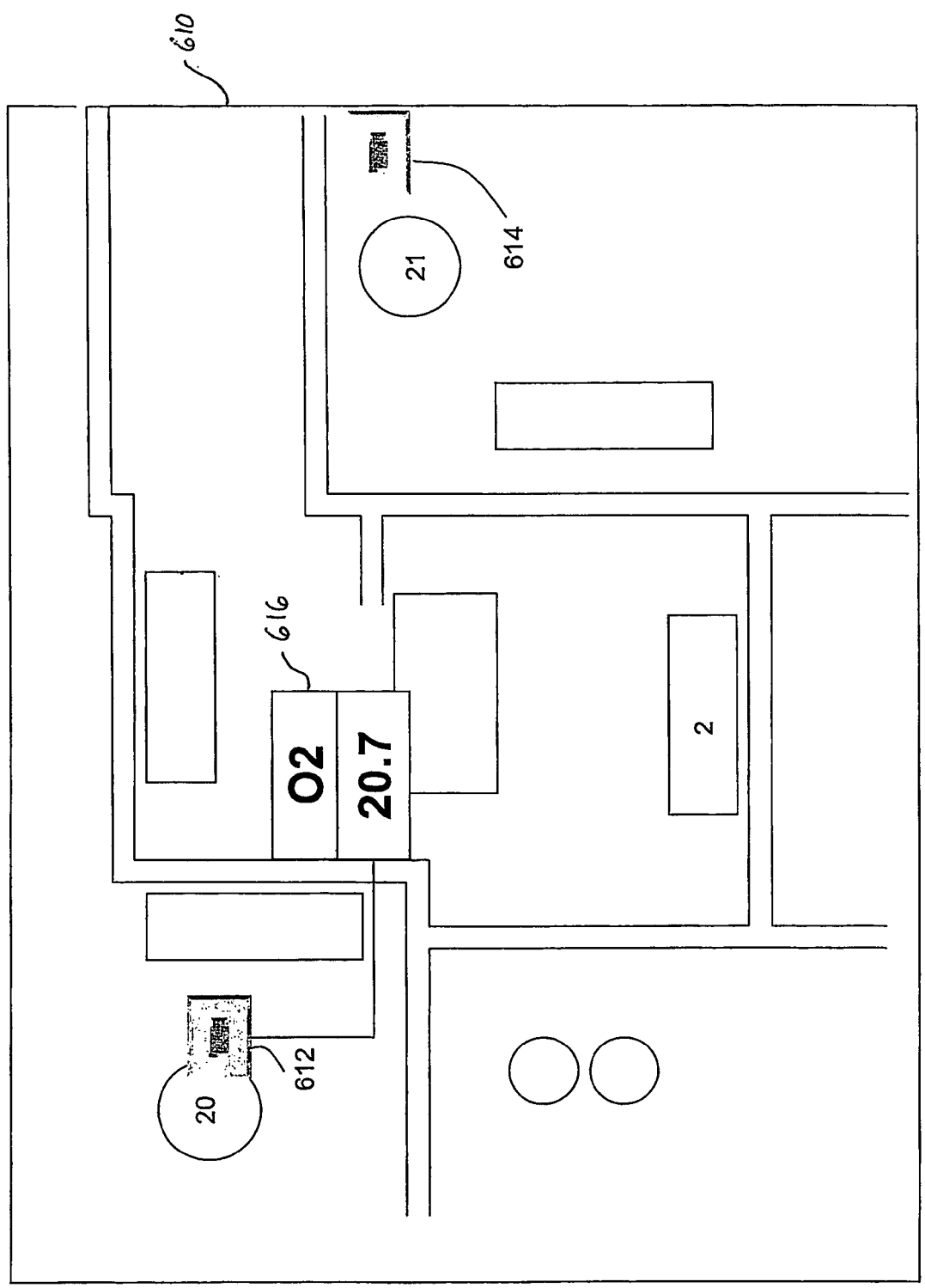
Figure 8:
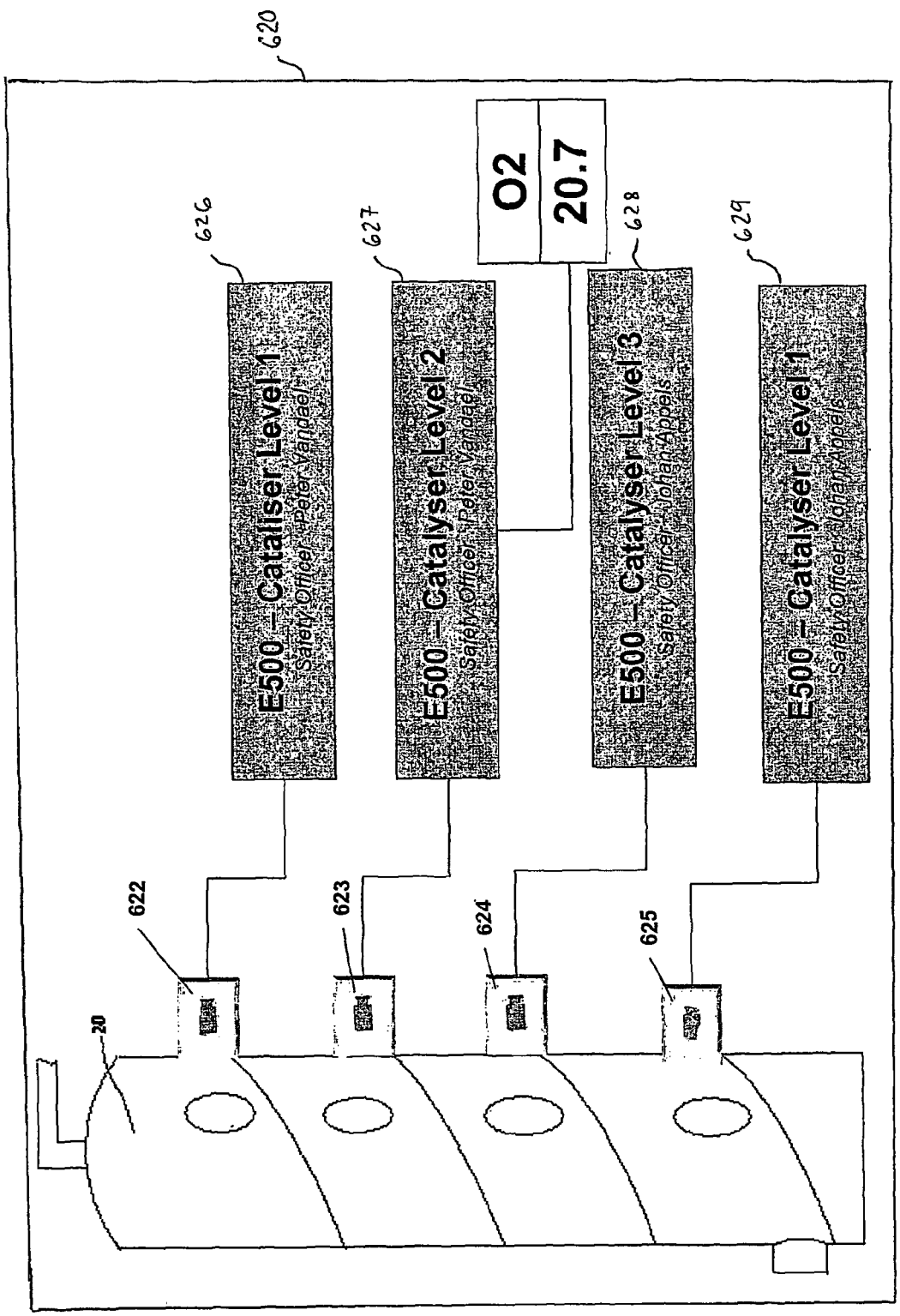

FIG. 7 indicates another view of primary screen 610. Processing unit 602, as mentioned above in conjunction with the description of the gas detection subsystem 200, is configured to compare the gas sensor data with limiting values. If any of these limits are exceeded, the processing unit 602 provides a warning signal on screen 610 in the form of a reading 616 of the measured value of the gas data and an indication of the location of the reading. Additional audible or visual warning signals may also be given. At this point, touching the screen at icon 612 will bring up secondary screen 620 as shown in FIG. 8. It should be noted that the operator can touch icon 612 to display secondary screen 620 at any point in time, independent of the presence of an alarm condition.

Secondary screen 620 gives a detailed overview of the situation at the column 20 including important structural and safety related details. Such information is also generally provided before commencing work at the site but may be updated as and when conditions change. Secondary screen 620 also includes further camera icons 622-625 which provides an indication of the location of the individual workplace units. For each of the icons 622-625 associated information 626-629 is provided relating to the identity of the workplace and the local safety officer responsible for that workplace. Processing unit 602 and secondary screen 620 may also be configured to provide additional information such as the presence or names of individual workers present in the column 20 at that moment. As mentioned above, this data is provided to the processing unit 602 by the access registration subsystem 400.

Figure 9:
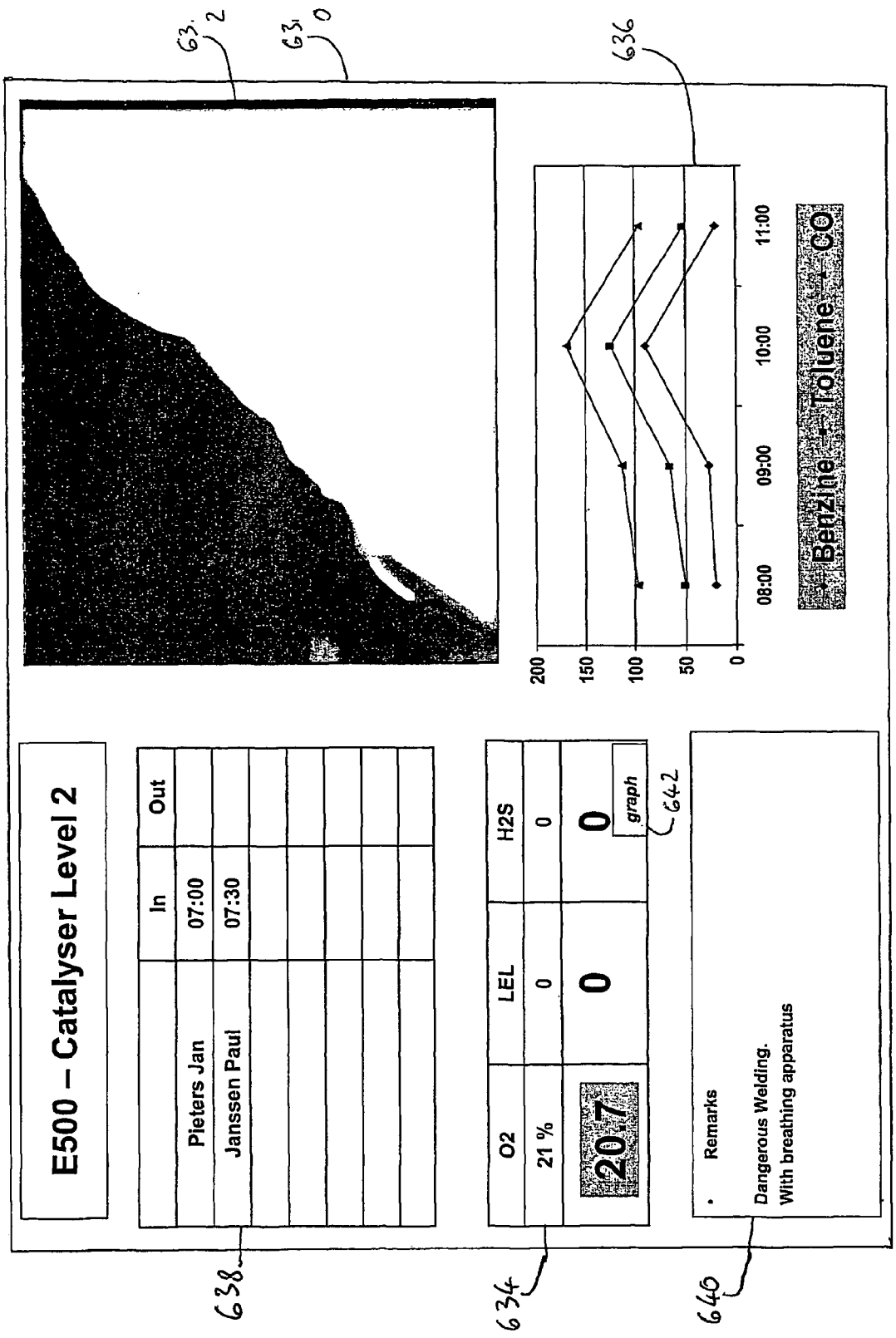

Touching any of the camera icons 622-625 on secondary screen 620 brings up data screen 630 as shown in FIG. 9. Data screen 630 provides the complete available data for the workplace 24b as provided by all appropriate sensors in the workplace module 5b. From video monitoring subsystem 100, data screen 630 receives a digital image 632 from video camera 102b via video converter 144. From gas sensor subsystem 200, data screen 630 receives local gas display 634 from local gas detectors 202b, 204b, 206b, which is displayed together with the limit values set for these gases. Extractive gas display 636 is also provided from extractive gas detector 242, giving the exposure of the workers to the monitored gases since the start of the shift. Access display 638 is also provided for data as received from access registration subsystem 400, which in FIG. 9 indicates that Jan Pieters has entered the workplace 24b at 07.00 and that Paul Janssen has entered at 07.30. Details display 640 gives further information regarding e.g. the nature of the work to be undertaken. This data may originate from the access registration subsystem 400 by reading from the individual cards. Alternatively it may be provided from other sources such as a central personnel database or a work coordination database associated with the issue of the cards to the workers.

Figure 10:
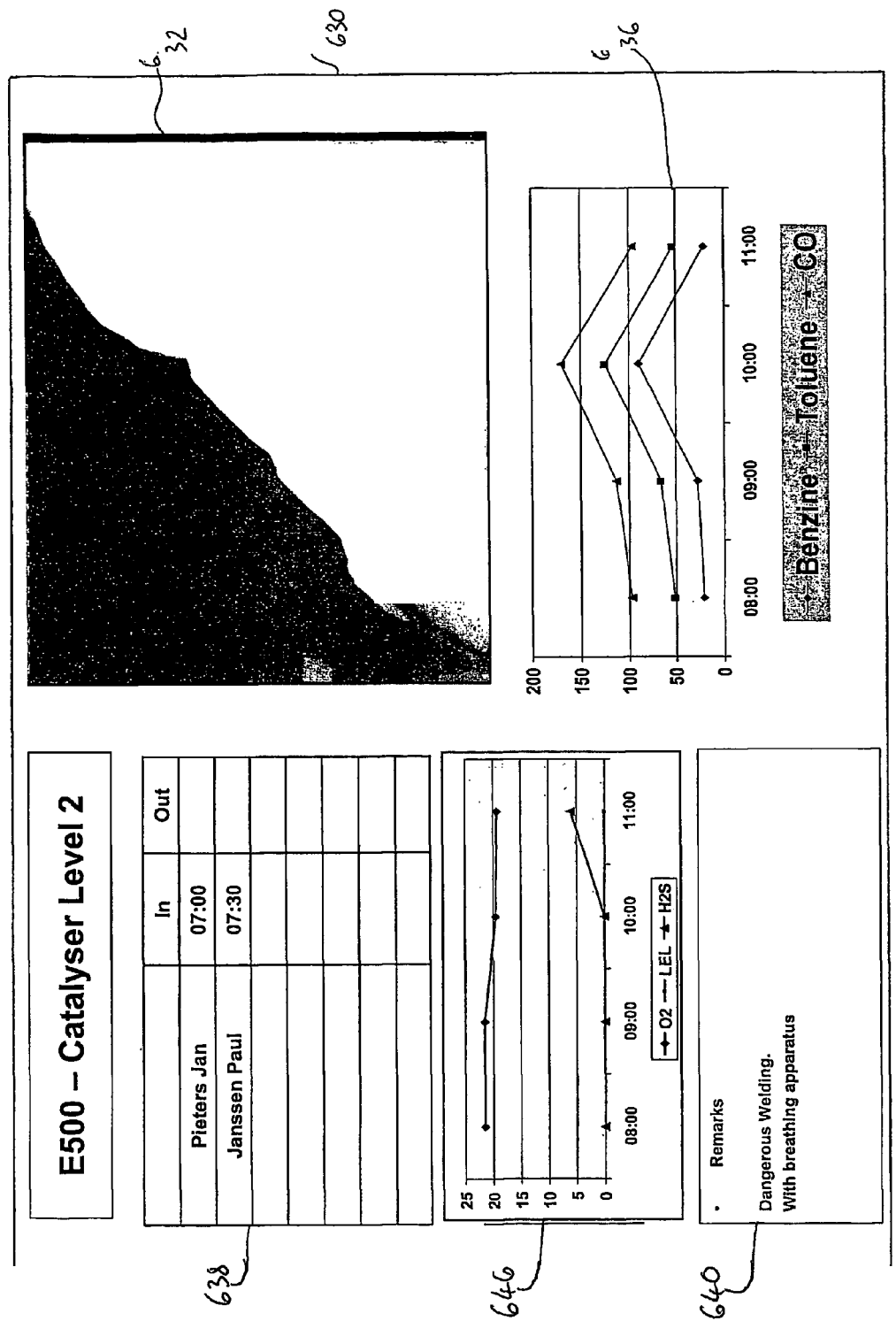
Figure 11:
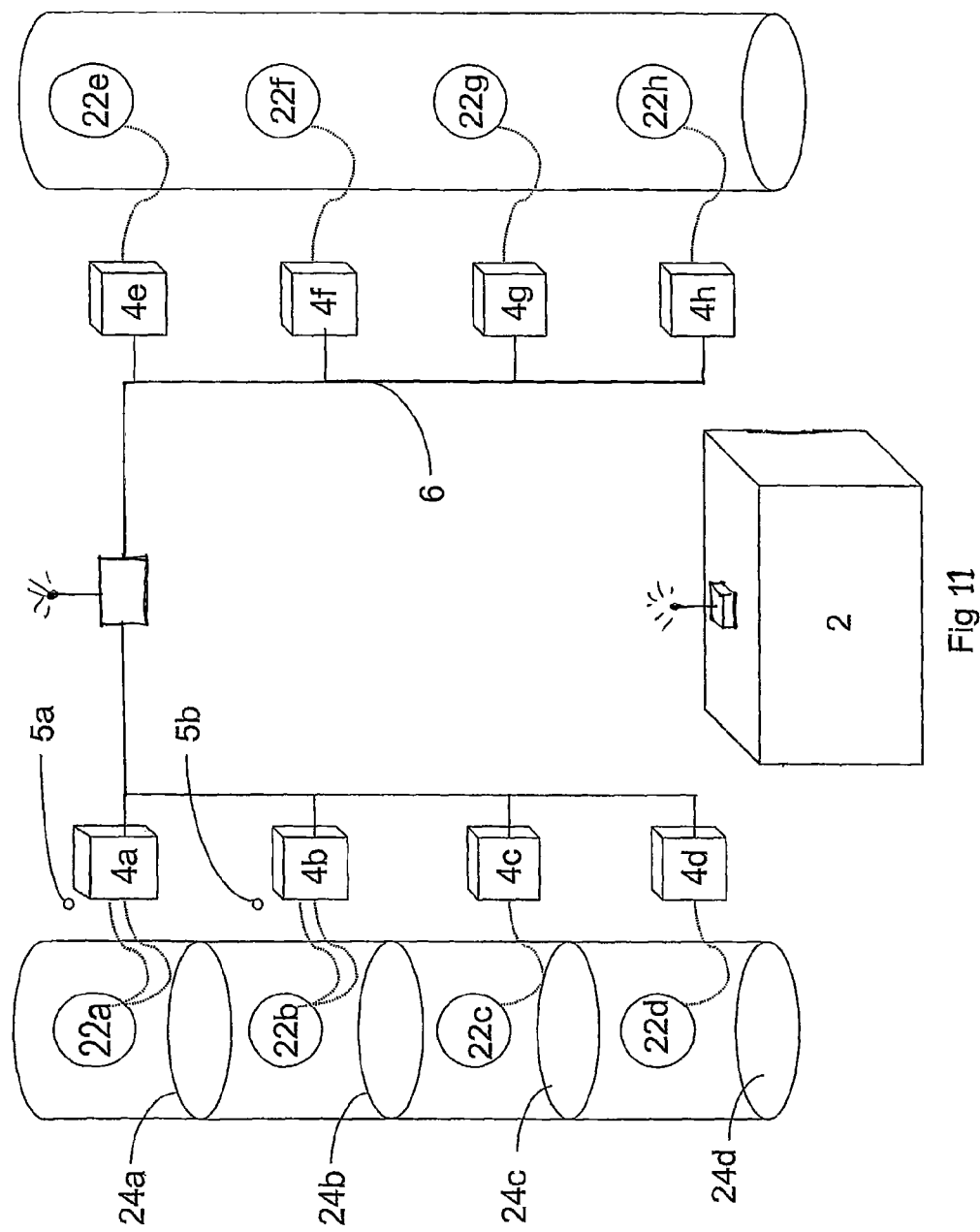
FIG. 11 is a schematic overview of a safety monitoring system having multiple workplaces modules according to the present invention.

FIG. 10 shows an alternative view of data screen 630. By touching icon 642 in FIG. 9, local gas display 634 is exchanged for a historical graph 646 indicating the evolution of the measured values from local gas detectors 202b, 204b, 206b.

Although the present invention has been described in the context of petrochemical columns and confined spaces, it is understood that the principles and the apparatus disclosed may also be applied to other situations where a mobile monitoring system may be required and that while the above examples illustrate preferred embodiments, various other arrangements may also be considered which fall within the spirit and scope of the present invention.

The invention claimed is:

1. A method of monitoring personnel operating at workplaces within confined spaces accessible via workplace access openings, the method comprising:
   for each workplace access opening, providing a selectively configurable mobile workplace module comprising a video registration device producing video data, an audio interface for emitting and receiving audio data, a gas sensor to produce gas sensor data and an isolation transformer supplying low voltage electrical power;
   mounting a workplace module adjacent to each workplace and at least partially within the confined spaces wherein the gas sensor is provided outside the confined space and gas from the workplace is transported to the gas sensor;
   providing a monitoring unit outside the workplaces and confined spaces, the monitoring unit comprising a display for displaying video data from the workplace modules, an audio interface for emitting and receiving audio data and a gas data receiver for receiving gas sensor data;
   connecting the workplace modules for signal transfer of data collected at each workplace to a transmitting station;
   transmitting data from the transmitting station to the monitoring unit; and
   monitoring at the monitoring unit the operation of personnel at the workplaces.

2. The method according to claim 1, wherein a workplace module comprises a presence detector and the method further comprises detecting the presence of a person at the workplace.

3. The method according to claim 2, wherein the presence detector comprises a workplace access registration device and the method further comprises registering the entry and exit of personnel into and from the confined space.

4. The method according to claim 2, wherein the presence detector comprises an identification device and the method further comprises identifying a person at a workplace and providing the identity to the monitoring unit.

5. The method according to claim 1, further comprising providing a recording device and recording data transmitted to the monitoring unit.

6. The method according to claim 1, further comprising comparing gas sensor data with predefined gas data limits and generating a warning in the event that the gas data limits are exceeded.

7. The method according to claim 1, further comprising at least one gas sensor is provided at a workplace.

8. The method according to claim 1, wherein the video registration device is controllable from the monitoring unit and the method further includes controlling the video registration device to zoom, pan or tilt.

9. A safety monitoring system for monitoring of workplaces within confined spaces accessible via workplace access openings, comprising:
   a plurality of selectively configurable mobile workplace modules each comprising a video registration device producing video data, an audio interface for emitting and receiving audio data, a gas sensor producing gas sensor data and wherein the gas sensor is an indirect as sensor for location at a distance from the workplace and outside the confined space, the gas sensor comprising a gas delivery channel for transporting gas from the workplace to the gas sensor and an isolation transformer supplying low voltage electrical power;
   a transmitting station, whereby each of the workplace modules is connected for signal transfer with the transmitting station; and
   a monitoring unit selectively connectable for data transmission between the transmitting station and the monitoring unit, the monitoring unit comprising a display for displaying video data from the workplace modules, an audio interface for emitting and receiving audio data and a gas data monitor for the gas sensor data.

10. The safety monitoring system according to claim 9, wherein the workplace modules further comprises a presence detector for detecting the presence of a person at a workplace.

11. The safety monitoring system according to claim 10, wherein the presence detector comprises a workplace access registration device for registering the entry and exit of personnel through a workplace access opening into and from the workplace.

12. The safety monitoring system according to claim 11, wherein the presence detector provides identification data to the monitoring unit, identifying the person at the workplace.

13. The safety monitoring system according to claim 11, wherein the workplace modules have an active state and a passive state, and the presence detector is active to cause transition of the workplace modules from the passive state to the active state in response to the detection of a person at the workplace.

14. The safety monitoring system according to claim 9, wherein the monitoring unit further comprises a recording device for recording data transmitted to the monitoring unit.

15. The safety monitoring system according to claim 9, wherein the gas data monitor compares gas sensor data with predefined gas data limits and generates a warning in the event that the gas data limits are exceeded.

16. The safety monitoring system according to claim 9, further comprising a direct gas sensor for location at a workplace.

17. The safety monitoring system according to claim 9, further comprising a mobile umbilical cable for connecting the workplace modules to the monitoring unit.

18. The safety monitoring system according to claim 17, wherein the mobile umbilical cable comprises an optical fibre for transmission of video data.

19. The safety monitoring system according to claim 9, wherein the workplace modules comprises a plurality of video registration devices.

20. A selectively configurable workplace module for a safety monitoring system comprising a workplace unit and a plurality of sensors, the workplace unit comprising a plurality of data interfaces for receiving data from the sensors and transmitting data to the safety monitoring system, a plurality of power outlets for providing electrical power to the sensors and an indirect gas sensor for location at distance from the work lace and outside the confined space, the gas sensor comprising a gas delivery channel for transporting gas from the workplace to the gas sensor.

21. The workplace module according to claim 20 whereby the workplace unit is adapted to transmit data to the safety monitoring system under Transmission Control Protocol/Internet Protocol (TCP/IP).

22. The workplace module according to claim 20 for a workplace in a confined space having a workplace access opening, wherein the workplace unit comprises a single workplace access registration device for registering the entry and exit of personnel into the confined space through said access opening.

23. The workplace module according to claim 20, wherein the sensors are each individually and independently connected to the workplace unit.

24. The safety monitoring system according to claim 9, wherein each mobile workplace module is connected to receive video data, audio data and gas sensor data from a single workplace.

25. The safety monitoring system according to claim 9, wherein each mobile workplace module comprises a workplace unit and a plurality of monitoring components and each monitoring component is independently connected to a respective interface with the workplace unit.

26. The safety monitoring system according to claim 11, wherein each mobile workplace module comprises one single workplace access registration device for registering the entry and exit of personnel to a single workplace.

27. The method according to claim 1, wherein each confined space comprises a single workplace access opening and each workplace unit is located adjacent to a respective workplace access opening.

* * * * *